United States Patent
Kerr et al.

[11] Patent Number: 6,065,342
[45] Date of Patent: May 23, 2000

[54] APPARATUS AND A METHOD OF LOCATING A SOURCE OF ACOUSTIC EMISSIONS IN AN ARTICLE

[75] Inventors: Noel C Kerr, Nottingham; John R Webster, Derby, both of United Kingdom

[73] Assignee: Rolls-Royce plc, London, United Kingdom

[21] Appl. No.: 09/158,136

[22] Filed: Sep. 22, 1998

[30] Foreign Application Priority Data

Oct. 1, 1997 [GB] United Kingdom .................... 9720720

[51] Int. Cl.$^7$ .............................. G01N 29/14; G01D 7/00
[52] U.S. Cl. ................................. 73/587; 73/801; 702/36; 367/127
[58] Field of Search ............................. 73/587, 584, 786, 73/801, 643; 702/36; 367/118, 125, 127, 128, 129; 706/31, 25

[56] References Cited

U.S. PATENT DOCUMENTS

| | | | |
|---|---|---|---|
| 3,875,381 | 4/1975 | Wingfield et al. | 73/587 |
| 3,985,024 | 10/1976 | Horak | 73/587 |
| 4,089,224 | 5/1978 | Scott et al. | 73/587 |
| 4,592,034 | 5/1986 | Sachse | 367/127 |
| 4,910,718 | 3/1990 | Horn | 367/124 |
| 4,979,124 | 12/1990 | Sachse | 364/507 |
| 5,010,503 | 4/1991 | Paton et al. | 73/587 |
| 5,115,681 | 5/1992 | Bouheraoua | 73/801 |
| 5,270,950 | 12/1993 | Cowley et al. | 73/587 |
| 5,505,090 | 4/1996 | Webster | 73/657 |
| 5,577,166 | 11/1996 | Mizuno | 395/22 |
| 5,924,986 | 7/1999 | Chandler et al. | 600/407 |

FOREIGN PATENT DOCUMENTS

| | | |
|---|---|---|
| 442207 A1 | 8/1991 | European Pat. Off. . |
| 0482 750 A1 | 4/1992 | European Pat. Off. . |
| 586054 A1 | 3/1994 | European Pat. Off. . |

*Primary Examiner*—Hezron Williams
*Assistant Examiner*—Helen C. Kwok
*Attorney, Agent, or Firm*—W. Warren Taltavull; Farkas & Manelli PLLC

[57] ABSTRACT

An apparatus (14) for locating a source of acoustic mission in an article (10) comprises a plurality of spaced transducers (18) which supply output signals corresponding to detected acoustic emission activity to a processor (24). Artificially induced acoustic emissions (12) are generated in the article (10) by directing a laser beam (33) onto the article (10). A camera (40) produces an image of the article (10) and any laser flashes. A processor (42) converts the positions of the laser flashes to coordinates on the article (10). A processor (24) analyses parameters of the acoustic emission in the output signals and the coordinates of the laser flashes to infer the mathematical relationship between the parameters and location of acoustic emissions. The same parameters for acoustic emissions of unknown source location are used to calculate the location of the unknown source with the deduced mathematical relationship and the calculated coordinates are converted by processor (42) to a position on the image produced by the camera (40) and the processor (24) provides an indication of the accuracy of the calculation.

30 Claims, 1 Drawing Sheet

APPARATUS AND A METHOD OF LOCATING A SOURCE OF ACOUSTIC EMISSIONS IN AN ARTICLE

FIELD OF THE INVENTION

The present invention relates to an apparatus and a method for locating a source of acoustic emissions in an article.

BACKGROUND OF THE INVENTION

Acoustic emissions, or stresswaves, arise in an article due to many different types of events, for example impacts of loose components on the article, a sudden movement of a defect, such as a crack, in the article or a sudden movement of an unbonded region between two joined components forming the article, by fibre breakage, matrix cracking and ply delaminations of composite material articles.

Previously sources of acoustic emission have been located by measuring the time of arrival of an acoustic emission pulse at each of several transducers. The difference in the times of arrival of the acoustic emission pulse at each of the transducers is calculated and triangulation techniques are used to deduce the location of the source of the acoustic emissions. The triangulation technique is generally performed analytically using complex, derived equations or by using look-up tables and interpolating. These derived equations are very difficult to derive for composite material articles or other articles with complex structures, because the relative velocity of sound in every direction must be calculated, i.e. composite material articles are anisotropic. This means that locating a source of acoustic emissions using triangulation techniques has to be set up by an acoustic emission expert. Commercially available systems for locating sources of acoustic emission are restricted to simple geometries such as flat plates, cylinders and spheres.

It is known to use neural networks to calculate the position of the source of an acoustic emission from published European Patent Application No 0482750A1 published Apr. 29, 1992. This document discloses measuring the times for the electrical output signals from each of the transducers to exceed two predetermined amplitudes from a datum time for artificially induced acoustic emission events having known locations to infer the mathematical relationship between values of time and location of the acoustic emission event. The times taken for the electrical output signals from the transducers to exceed the two predetermined amplitudes for an acoustic emission event of unknown location are measured and the neural network uses the inferred mathematical relationship to calculate the location of the unknown source.

It is known to artificially induce acoustic emissions by breaking a pencil lead against the article or by directing a laser beam onto the surface of the article.

A problem with the apparatus using neural networks for locating a source of acoustic emissions in an article is that they require an acoustic emission experts to set up and teach the neural network to infer the mathematical relationship between values of time and location of the acoustic emission event.

SUMMARY OF THE INVENTION

The present invention seeks to provide an apparatus for locating a source of acoustic emissions in an article which overcomes the above mentioned problem.

Accordingly the present provides an apparatus for locating a source of acoustic emissions in an article comprising at least one transducer acoustically coupled to the article, the or each transducer being arranged to detect acoustic emissions in the article and being arranged to produce a corresponding output signal, means to produce a plurality of artificially induced acoustic emission events having known locations on the article, means to view the article and the locations of any artificially induced acoustic emission events to produce an image of the article and the locations of any artificially induced acoustic emission events, means to extract parameters from the output signals, means for analysing the image of the article and any artificially induced acoustic emission events to determine the coordinates of the locations of artificially induced acoustic emission events on the article, means for analysing the parameters extracted from the output signals and the coordinates of the corresponding locations of the artificially induced acoustic emission events to infer the mathematical relationship between the extracted parameters and the location of a source of an acoustic emission event, means for storing the deduced mathematical relationship, means for calculating from the parameters extracted from the electrical output signals for an acoustic emission event of unknown source location and the stored mathematical relationship the location of the source of the acoustic emission event.

Preferably there are means to display the calculated location of the source of the acoustic emission event on an image of the article.

There may be means to display the calculated location of the source of the unknown acoustic emission event on a mathematical model of the article.

There may be means to display the location of the artificially induced acoustic emission event on a mathematical model of the article.

Preferably the means to view the article is a video camera.

Preferably the means to produce artificially induced acoustic emission comprises a laser and means to direct a laser beam onto the article at the plurality of locations. Alternatively a breaking pencil lead or particle impacts may be used.

The means for analysing the parameters and the coordinates of the corresponding locations of the artificially induced acoustic emission events may comprise a neural network.

The means for calculating from the parameters and the stored mathematical relationship may comprise a neural network.

The neural network may have a plurality of output neurons, a number of the neurons indicate the coordinates of the location of the acoustic emission event and at least one of the neurons indicates the accuracy of the calculation of the coordinates of the location of the acoustic emission event.

The means for calculating from the parameters and the stored mathematical relationship may comprise a lookup table.

The present invention also provides a method of locating a source of acoustic emissions in an article comprising generating a plurality of artificially induced acoustic emission events having known locations on the article, detecting the plurality of artificially induced acoustic emission events at at least one transducer acoustically coupled to the article, viewing the article and the locations of any artificially induced acoustic emission events, producing an image of the article and the locations of any artificially induced acoustic emission events, extracting parameters from the output signals of the transducers, analysing the image of the article and any extracted parameters of any artificially induced acoustic emission events to determine the coordinates of the location of the artificially induced acoustic emission events on the article, analysing the parameters extracted from the output signals of the transducers and the coordinates of the corresponding location of the artificially induced acoustic emission events to infer the mathematical relationship between the extracted parameters and the location of a source of an acoustic emission event, storing the deduced mathematical relationship, calculating from the parameters extracted from the output signals of the transducers for an acoustic emission event of unknown source location and the stored mathematical relationship the location of the source of the acoustic emission event.

The neural network may be used to analyse differences in arrival times of the acoustic emission pulse at the transducers for artificially induced acoustic emission events having known locations to infer the mathematical relationship between the arrival time differences and the location of the acoustic emission event. The neural network is then used to calculate the location of an acoustic emission event of unknown source location. During the training of the neural network, in which the mathematical relationship is deduced, the training data is generated in a controlled manner such that the signal to noise ratio in the electrical output signals is high to enable the arrival times of the acoustic emission pulse at the transducers to be detected easily and accurately. However, during monitoring of the article when loaded or fatigued the acoustic emissions generated have varying amplitudes and characteristics. In the case of a composite material article, the material has very high attenuation and this makes any acoustic emission event appear different at each of the transducers if the paths travelled by the acoustic emission to them have different lengths. Composite material articles are also dispersive which causes the leading edge of the acoustic emission to be spread out in time. These two factors together make the detection of the arrival times of the acoustic emission pulse at the transducers more difficult and less accurate.

Thus the neural network does not know that there may be errors in the differences in times of arrival and gives an answer regardless. This results in a loss of accuracy in the x-y coordinates, and a spreading of results around what could ideally be one particular localised source location. In the case of composite material articles, matrix failure at low loads may be expected to be randomly distributed over the whole structure. However, but for the errors mentioned above, certain areas of the article may have had a series of acoustic emission events grouped together. A grouping together of acoustic emission events is likely to be a precursor of ultimate structural failure and is of great importance.

The present invention also seeks to provide an apparatus for locating a source of acoustic emission in an article which validates the accuracy of its calculation.

Accordingly the present invention provides an apparatus for locating a source of acoustic emissions in an article comprising at least one transducer acoustically coupled to the article, the or each transducer being arranged to detect acoustic emissions in the article and being arranged to produce a corresponding output signal, means to extract parameters from the output signals, means for analysing the parameters extracted from the output signals for a plurality of artificially induced acoustic emission events having known locations to infer the mathematical relationship between the extracted parameters and the location of a source of an acoustic emission event, means for storing the deduced mathematical relationship, means for calculating from the parameters extracted from the electrical output signals for an acoustic event of unknown source location and the stored mathematical relationship the location of the source of the acoustic emission event, the means for analysing and the means for calculating is a neural network, the neural network having a plurality of output neurons, a number of the output neurons indicate the location of the source of the acoustic emission event and at least one of the output neurons indicates the accuracy of the calculation of the location of the source of the acoustic emission event.

Preferably there are means to produce a plurality of artificially induced acoustic events having known locations on the article, means to view the article and the locations of any artificially induced acoustic emission events to produce an image of the article and the locations of any artificially induced acoustic emission events, means for analysing the image of the article and any artificially induced acoustic emission events to determine the coordinates of the locations of the artificially induced acoustic events on the article, the analysing means analyses the parameters extracted from the output signals and the coordinates of the corresponding locations of the artificially induced acoustic emission events.

Preferably there are means to display the image of the article and the location of the artificially induced acoustic emission events on the image of the article.

Preferably there are means to display the calculated location of the source of an acoustic emission event on an image of the article.

Preferably the means to produce artificially induced acoustic emission events comprises a laser and means to direct a laser beam onto the article at a plurality of locations. Alternatively a breaking pencil lead or particle impacts may be used.

The means to extract parameters may measure the differences in arrival times of the acoustic emission events at each one of a plurality of transducers.

The present invention also provides a method of locating a source of acoustic emissions in an article comprising generating a plurality of artificially induced acoustic emission events having known locations on the article, detecting the plurality of artificially induced acoustic emission events at at least one transducer acoustically coupled to the article, extracting parameters from the output signals of the transducers, introducing errors into the parameters extracted for at least one of the artificially induced acoustic emission events, analysing the parameters extracted from the output signals of the plurality of artificially induced acoustic emission events having known locations and any introduced errors in the parameters using a neural network to infer the mathematical relationship between the extracted parameters and the location of a source of an acoustic emission event, storing the deduced mathematical relationship, calculating from the parameters extracted from the output signals for an acoustic emission event of unknown source location and the stored mathematical relationship using the neural network the location of the source of the emission event and the accuracy of the calculation of the location of the source of the acoustic emission event.

BRIEF DESCRIPTION OF THE DRAWINGS

The present invention will be more fully described by way of example with reference to the accompanying drawings in which.

DETAILED DESCRIPTION OF THE INVENTION

Figure 1:
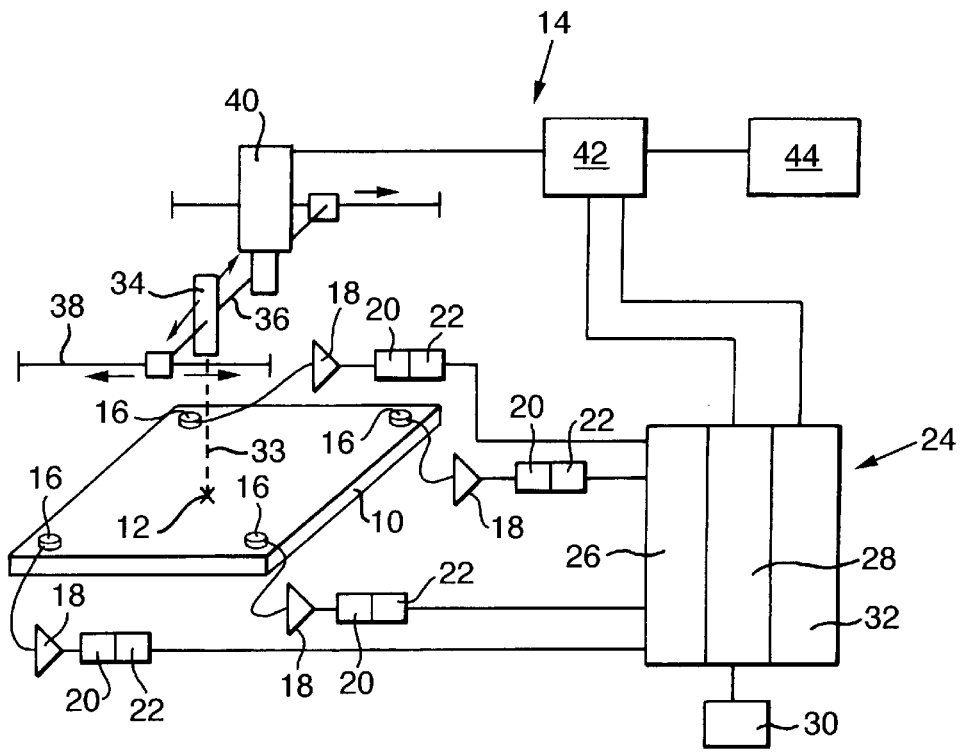
FIG. 1 is an apparatus for locating a source of acoustic emission in an article according to the present invention and FIG. 2 is a schematic view of a neural network for use in the present invention.

An apparatus 14 for locating a source of acoustic emission in an article 10, shown in FIG. 1, comprises at least one transducer, for example four spaced apart transducers 16 acoustically coupled to the article 10. Each transducer 16 is arranged to detect acoustic emissions or stresswaves, generated in the article 10 as a result of an impact, by frictional processes, produced by sudden movement of a defect such as a crack or an unbonded region between two joined components forming the article 10, by fibre breakage, by matrix cracking or by ply delaminations of composite materials. Each transducer 16 is acoustically coupled to the article by a suitable grease, adhesive or other acoustic couplants well known in the art. Each transducer 16 is arranged to produce an electrical output signal dependent upon the acoustic emission activity detected. The transducers 16 are commonly piezoceramic elements, although other suitable types of transducers may be used.

The electrical output signal produced by each transducer 16 is supplied to a respective amplifier 18. Each amplifier 18 amplifies the respective electrical output signal and each amplifier 18 may have filters to select the required frequency band or frequency bands.

In this example each amplified electrical output signal is rectified by a rectifier 20 and is then supplied to a signal enveloper 22 which envelopes the rectified electrical output signal. As an example the enveloper 22 envelopes the rectified electrical output signal with a 100 micro second time constant, although other suitable time constants may be used. Each rectified electrical output signal is supplied to a processor 24. The processor 24 processes the enveloped electrical output signals to locate the source of an acoustic emission event.

Alternatively the electrical output signal from each transducer after amplification and filtering may be supplied to the processor 24. The processor 24 processes the output signals to locate the source of an acoustic emission event.

The processor 24 comprises a plurality of time of arrival detection devices and a measuring device 26 which measures the relative time differences between the times of arrival of an acoustic emission wave front from an acoustic emission event for each pair of transducers 16 in the array. Thus for example for four transducers there are six relative time differences measured. The processor 24 also comprises an analysing device 28, for example a neural network, a software implementation of a neural network, a look up table or other suitable mathematical method, for analysing the differences in times of arrival of the electrical output signals.

A neural network is a pattern recognition and classification technique which has been described in many publications, for example "An artificial Neural Network Tutorial—Part 1—Basics" by K N Karma and D M Breen published in "The International Journal of Neural Networks" Volume 1, number 1, January 1989.

The neural network 28 is trained by generating a number of artificially induced acoustic emission events 12, at a number of different known locations in the article 10. The artificially induced acoustic emission events 12 are produced by directing a laser beam 33 from a laser gun 34 upon any suitable surface, or surfaces, of the article 10. The laser beam 33 is directed to impinge upon the surface of the article 10 at different locations by moving the laser gun 34 relative to the article 10 along two mutually perpendicular tracks 36 and 38. Alternatively, it would be possible to cause the laser beam 33 to strike different locations on the surface of the article 10 by controlled deflection of the laser beam 33 using mirrors. It may also be possible to move the article 10 relative to the laser beam 33.

The locations of these artificially induced acoustic emission events 12 are known and these are used as the desired outputs of the neural network 28 for training purposes. The relative time differences between the times of arrival of the acoustic emission wave front from each artificially induced acoustic emission event 12 for each pair of transducers 16 is supplied by the measuring device 26 to the neural network 28 as the inputs to the neural network 28 for training purposes. The neural network 28 infers, or deduces the mathematical relationship between the inputs and the desired outputs.

The processor 24 also has a store 30 in which the mathematical relationship, correlation or knowledge, inferred by the neural network 28 is stored in the form of a key matrix of values, known as the input signal weights.

Once the neural network 28 has been trained, and the mathematical relationship is held in the store 30, the relative time differences between the times of arrival of the acoustic emission wave front from an acoustic emission event of unknown source location for each pair of transducers 16 is supplied by the measuring device 26 to the neural network 28 and these are used with the stored mathematical relationship to calculate the location of the acoustic emission source.

A video camera 40 is arranged to view the surface of the article 10 to produce an image of the article 10. The image of the article 10 is supplied to a processor 42 which operates on the image of the article 10 in two different modes.

In the first mode the neural network 28 is being trained, the processor 42 analyses the image of the article 10 and the locations of the artificially induced acoustic emission events 12 which correspond to the points where the laser beam 33 strikes the article 10. The pixel position of the flash where the laser beam strikes the article 10, in the image of the article 10, corresponds to a known surface coordinate on the article 10. The processor 42 converts the pixel positions of the flashes to the surface coordinates on the article 10 and supplies the surface coordinates of the flashes, which correspond to the locations of the artificially induced acoustic emission events 12 to the neural network 28.

In the second mode, after the neural network 28 has been trained, the processor 42 receives the surface coordinates of the acoustic emission event of unknown source location from the neural network 28 via a processor 24 output 32. The processor 42 converts the surface coordinates of the acoustic emission event of unknown source location to a pixel position on the video image of the article 10.

In both modes of operation, the image of article 10 is supplied to a visual display unit 44 so that in the first mode of operation the article 10 and the laser beam flashes are displayed and in the second mode of operation the image of the article 10 and the location of an unknown acoustic emission event are displayed. In the first mode of operation the processor 42 may supply the surface coordinates of the flashes, which correspond to the locations of the artificially induced acoustic emission events 12 to a mathematical model of the article 10 such that the position of the artificially induced acoustic emission events is indicated in the mathematical model of the article 10. In the second mode of operation the processor 42 may supply the coordinates of the acoustic emission events of unknown source location to the mathematical model of the article 10 such that the position of the acoustic emission events of unknown source location are indicated in the mathematical model of the article 10.

The advantage of this method is that it enables the location of acoustic emissions to be detected simply and quickly without detailed knowledge of the geometry of the article 10 or the material characteristics of the article 10. During the training mode the locations of the artificially induced acoustic emission events are automatically supplied to the neural network.

During training of the neural network data are generated in a controlled way such that the signal to noise ratio of the artificially induced acoustic emission wave front in the electrical output signals is very high and thus the arrival detection devices 26 produce very accurate arrival time differences. However, during testing of the article 10 the signal to noise ratio of the acoustic emission wave front in the electrical signal is much smaller and thus the arrival detection devices 26 produce less accurate arrival time differences. The reason for the lower signal to noise ratio of the acoustic emission wave front is, in the case of a composite material due to very high attenuation and different path lengths and also dispersion which tends to draw out the leading edge of the acoustic emission wave front. A simply trained neural network has no way of knowing that the time difference data is in error and gives coordinates for the source location of the acoustic emission regardless.

Figure 2:
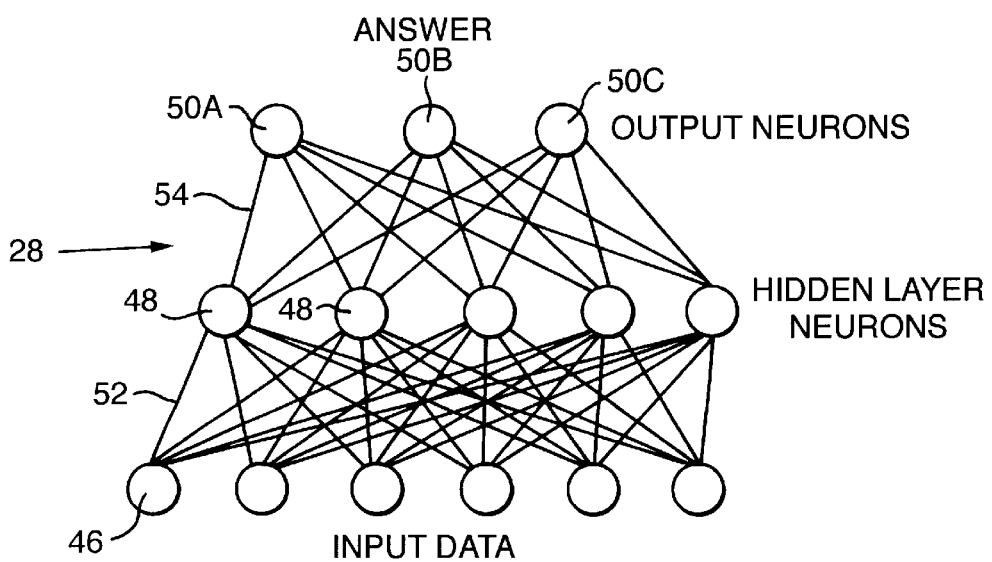

A neural network 28 suitable for the present invention, shown schematically in FIG. 2, comprises a first, or input, layer of neurons 46 which receives data to be processed, a second, or hidden, layer of neurons 48 and a third, or output, layer of neurons 50 which outputs the answer. Interconnecting each of the neurons 46 to each of the neurons 48 are first weighted interconnections 52 and interconnecting each of the neurons 48 to each of the neurons 50 are second weighted interconnections 54.

A further feature of the present invention is that the neural network 28 also indicates the accuracy of the calculation of the coordinates of an acoustic emission event of unknown source location.

The neural network 28 comprises a plurality of output neurons, n+m output neurons where n output neurons indicate the coordinates of the acoustic emission event and m output neurons indicate the accuracy of the calculation of the coordinates. In this example there are three output neurons 50A, 50B and 50C, the first and second output neurons 50A and 50B indicate the coordinates of the acoustic emission event, and the third output neuron 50C indicates the accuracy of the calculation of the coordinates.

Thus during the training mode for the neural network 28 a first set of training data is supplied to the input neurons 46 of the neural network 28 with very high signal to noise ratio and this is assumed to be perfect data, together with the coordinates of the artificially induced acoustic emission events to the output neurons 50A and 50B and also with a value of 1 to the output neuron 50C to indicate high accuracy. Knowing the desired accuracy of the calculated coordinates and the velocity of sound in the article 10 it is possible to calculate what time difference will result in this error. A second set of training data is supplied to the input neurons 46 which has the time error either added or subtracted randomly from the input neurons 46, together with the coordinates of the artificially induced acoustic emission events to the output neurons 50A and 50B and also with a value of 0 to the output neuron 50C to indicate low accuracy.

During testing of the article 10 the neural network 26 also has the third output neuron 50C which gives an additional output valued between 0 and 1 as well as the coordinates of the source of the acoustic emission event. The value of the third output neuron 50C relates to the error in measuring the difference in the arrival times. If there are large errors the neural network 26 assigns a value near 0, if there are small errors the neural network assigns a value near 1. Thus the neural network 26 indicates the accuracy of the calculation of the coordinates of the source of the acoustic emission event.

Although the description refers to producing the artificially induced acoustic emission events using a laser beam directed onto the article, it may be possible to use other suitable methods, for example breaking a pencil lead, electric discharge or particle impacts, which may be viewed by a video camera to calculate the coordinates of the artificially induced acoustic emission events.

Although the description refers to detecting arrival times of the acoustic emissions at the transducers and measuring differences in arrival times, it is equally possible to use other suitable parameters from the electrical output signals of the transducers for example the relative times to equal or exceed at least two predetermined amplitudes, the times to reach maximum amplitudes etc.

Although the description refers to four spaced transducers it is possible to use three or more spaced transducers with difference in times of arrival.

Alternatively, one or more transducers may be used with difference in times of arrival of individual acoustic emission reflections from the surfaces of the article.

The mathematical model may be a computer aided design (CAD) or finite element package.

We claim:

1. An apparatus for locating a source of acoustic emissions in an article comprising at least one transducer acoustically coupled to the article, said at least one transducer being arranged to detect acoustic emissions in the article and being arranged to produce a corresponding output signal, means to produce a plurality of artificially induced acoustic emission events having known locations on the article, camera means to view the article and the locations of any artificially induced acoustic emission events to produce an image of the article and the locations of any artificially induced acoustic emission events, means to extract parameters from the output signals, means for analysing the image of the article and any artificially induced acoustic emission events to determine the coordinates of locations of artificially induced acoustic emission events on the article, means for analysing the parameters extracted from the output signals and the coordinates of the corresponding locations of the artificially induced acoustic emission events to infer a mathematical relationship between the extracted parameters and a location of a source of an acoustic emission event, means for storing the deduced mathematical relationship, means for calculating from the parameters extracted from the output signals for an acoustic emission event of unknown source location and the stored mathematical relationship the location of the unknown source of the acoustic emission event.

2. An apparatus as claimed in claim 1 comprising means to display the calculated location of the source of the acoustic emission event on an image of the article.

3. An apparatus as claimed in claim 1 comprising means to display the location of the source of the unknown acoustic emission event based on a mathematical model of the article.

4. An apparatus as claimed in claim 1 comprising means to display the locations of the artificially induced acoustic emission events on a mathematical model of the article.

5. An apparatus as claimed in claim 1 in which the means to view the article is a video camera.

6. An apparatus as claimed in claim 1 in which the means to produce artificially induced acoustic emission events comprises a laser and means to direct a laser beam onto the article at a plurality of locations.

7. An apparatus as claimed in claim 1 in which the means for analysing the parameters and the coordinates of the corresponding locations of the artificially induced acoustic emission events comprises a neural network.

8. An apparatus as claimed in claim 1 in which the means for calculating from the parameters and the stored mathematical relationship comprises a neural network.

9. An apparatus as claimed in claim 7 or claim 8 in which the neural network has a plurality of output neurons, a number of the neurons indicate the coordinates of the locations of the acoustic emission events and at least one of the neurons indicates the accuracy of the calculation of the coordinates of the locations of an acoustic emission events.

10. An apparatus as claimed in claim 1 in which the means for calculating from the parameters and the stored mathematical relationship comprises a lookup table.

11. An apparatus as claimed in claim 1 in which the means to extract parameters measures the time taken for each of the output signals to equal or exceed at least one predetermined amplitude.

12. An apparatus as claimed in claim 11 in which the means to extract parameters measures the time taken for each of the electrical output signals to equal a peak amplitude.

13. An apparatus as claimed in claim 1 in which the means to extract parameters measures a differences in arrival times of the acoustic emission events at each one of a plurality of transducers, or differences in arrival times at a single transducer.

14. An apparatus as claimed in claim 1 comprising means to display the image of the article and the location of the artificially induced acoustic emission events.

15. A method of locating a source of acoustic emissions in an article comprising generating a plurality of artificially induced acoustic emission events having known locations on the article, detecting the plurality of artificially induced acoustic emission events at a plurality of tranducers each acoustically coupled to the article and which produce output signals, viewing the article with a camera and the locations of any artificially induced acoustic emission events, producing an image of the article and the locations of any artificially induced acoustic emission events, extracting parameters from the output signals of the transducers, analysing the image of the article and any extracted parameters of any artificially induced acoustic emission events to determine the coordinates of a location of the artificially induced acoustic emission events on the article, analysing the parameters extracted from the output signals of the transducers and the coordinates of the corresponding location of the artificially induced acoustic emission events to infer a mathematical relationship between the extracted parameters and the location of a source of an acoustic emission event, storing the deduced mathematical relationship, calculating from the parameters extracted from the output signals of the transducers for an acoustic emission event of unknown source location and the stored mathematical relationship the location of the unknown source of the acoustic emission event.

16. A method as claimed in claim 15 comprising displaying the calculated location of the source of the acoustic emission event on an image of the article.

17. A method as claimed in claim 15 comprising displaying the location of the source of the unknown acoustic emission event on a mathematical model of the article.

18. A method as claimed in claim 15 comprising displaying the locations of the artificially induced acoustic emission events on a mathematical model of the article.

19. A method as claimed in claim 15 comprising viewing the article using a video camera.

20. A method as claimed in claim 15 comprising producing the artificially induced acoustic emission event by directing a laser beam, by breaking pencil lead, by impacting particles onto the article at a plurality of locations.

21. A method as claimed in claim 15 comprising analysing the parameters and the coordinates of the corresponding locations using a neural network.

22. A method as claimed in claim 15 comprising calculating the location of the source of the acoustic emission event using a neural network.

23. A method as claimed in claim 21 or claim 22 comprising indicating an accuracy of the calculation of the coordinates of the locations of the acoustic emission events.

24. A method as claimed in claim 15 wherein the extracting of parameters from the output signals of the transducers comprises measuring the time taken for each of the electrical output signals to equal or exceed at least one predetermined amplitude.

25. A method as claimed in claim 15 wherein the extracting of parameters from the output signals of the plurality of transducers comprises measuring a differences in arrival times of the acoustic emission events at the transducers.

26. A method as claimed in claim 15 comprising displaying the image of the article and locations of the artificially induced acoustic emission events.

27. An apparatus for locating a source of acoustic emissions in an article comprising at least one transducer acoustically coupled to the article, said transducer being arranged to detect acoustic emissions in the article and being arranged to produce a corresponding output signal, means to extract parameters from the output signals, means for analysing the parameters extracted from the output signals for a plurality of artificially induced acoustic emission events having known locations to infer a mathematical relationship between the extracted parameters and the location of a source of an acoustic emission event, means for storing the deduced mathematical relationship, means for calculating from the parameters extracted from the electrical output signals for an acoustic event of unknown source location and the stored mathematical relationship the location of the source of the acoustic emission event, the means for analysing and the means for calculating being a neural network, the neural network having a plurality of output neurons, a number of the output neurons indicating the location of the source of the acoustic emission event and one of the output neurons indicating the accuracy of the calculation of the location of the source of the acoustic emission event.

28. An apparatus as claimed in claim 27 comprising means to produce a plurality of artificially induced acoustic events having known locations on the article, means to view the article and the locations of any artificially induced acoustic emission events to produce an image of the article and the locations of any artificially induced acoustic emission events, means for analysing the image of the article and any artificially induced acoustic emission events to determine the coordinates of the locations of the artificially induced acoustic events on the article, the analysing means analysing the parameters extracted from the output signals and the coordinates of the corresponding locations of the artificially induced acoustic emission events.

29. A method of locating a source of acoustic emissions in an article comprising generating a plurality of artificially induced acoustic emission events having known locations on the article, detecting the plurality of artificially induced acoustic emission events at at least one transducer acoustically coupled to the article, and producing output signals extracting parameters from the output signals of the transducers, introducing errors into the parameters extracted for at least one of the artificially induced acoustic emission events, analysing the parameters extracted from the output signals of the plurality of artificially induced acoustic emission events having known locations and any introduced errors in the parameters using a neural network to infer a mathematical relationship between the extracted parameters and a location of a source of an acoustic emission event, storing the deduced mathematical relationship, calculating from the parameters extracted from the output signals for an acoustic emission event of unknown source location and the stored mathematical relationship using the neural network the location of the source of the emission event and an accuracy of the calculation of the location of the source of the acoustic emission event.

30. A method as claimed in claim 29 comprising viewing the article and the locations of any artificially induced acoustic emission events, producing an image of the article and the location of any artificially induced acoustic emission events, analysing the image of the article and any artificially induced acoustic emission events to determine the coordinates of the locations of the artificially induced acoustic emission events on the article, analysing the parameters extracted from the output signals and the coordinates of the corresponding locations of the artificially induced acoustic emission events.

* * * * *